US005654423A

United States Patent [19]
Kahl et al.

[11] Patent Number: 5,654,423
[45] Date of Patent: *Aug. 5, 1997

[54] BORONATED METALLOPORPHYRINE AND THERAPEUTIC METHODS

[75] Inventors: Stephen B. Kahl, Portola Valley; Myoung-Seo Koo, San Francisco, both of Calif.

[73] Assignee: Regents of the University of California, Oakland, Calif.

[*] Notice: The term of this patent shall not extend beyond the expiration date of Pat. No. 5,149,801.

[21] Appl. No.: 448,225

[22] Filed: May 23, 1995

Related U.S. Application Data

[63] Continuation of Ser. No. 130,302, Oct. 1, 1993, abandoned, which is a continuation-in-part of Ser. No. 940,095, Sep. 3, 1992, abandoned, and Ser. No. 869,611, Apr. 16, 1992, Pat. No. 5,284,831, which is a division of Ser. No. 616,679, Nov. 21, 1990, Pat. No. 5,149,801, said Ser. No. 940,095, is a continuation-in-part of Ser. No. 616,679.

[51] Int. Cl.$^6$ .................................................. C07D 487/22
[52] U.S. Cl. ........................................ 540/145; 534/15
[58] Field of Search ............................ 534/15; 540/145; 424/1.65, 9; 514/64, 410, 499, 501

[56] References Cited

U.S. PATENT DOCUMENTS

| | | | |
|---|---|---|---|
| 4,516,535 | 5/1985 | Russell, Jr. et al. | 128/1.1 |
| 4,959,356 | 9/1990 | Miura et al. | 540/145 |
| 4,963,655 | 10/1990 | Kinder et al. | 548/110 |
| 5,015,478 | 5/1991 | Jori et al. | 514/410 |
| 5,109,016 | 4/1992 | Dixon | 540/145 |
| 5,128,319 | 7/1992 | Arlinghaus | 514/14 |
| 5,132,291 | 7/1992 | Gruber | 514/50 |
| 5,149,801 | 9/1992 | Kahl et al. | 540/145 |
| 5,284,831 | 2/1994 | Kahl et al. | 514/21 |

OTHER PUBLICATIONS

Koenig, S. H. et al., Magn. Reson. Med., vol. 4(3), pp. 252–260, 1987, BIOSIS; 87:256886.

Lyon, R. C. et al, Magn. Reson. Med., vol. 4(1), pp. 24–33, 1987, CA; 106(17): 134584j.

Pantchides, M.L. et al., "The uptake of porphyrin & Zinc metalloporphyrin" . . . Photochem. Photobiol., vol. 57(5), pp. 838–841, 1993. CA 119(13):134468t.

Smith, Kevin M., et al., "The NMR Spectra of porphyrins . . . ", Tetrahedron vol. 38(15), pp. 2441–2449, 1982. CA 98(23):197476n.

Barth et al., "Boron Neutron Capture Therapy for Cancer", Scientific American, 100–107, Oct. 1990.

Coderre et al., "Selective Delivery of Boron by the Melanin Precursor Analogue p–Boronophenylalanine to Tumors Other Than Melanoma", Cancer Research, 50, 138–141, Jan. 1, 1990.

Delaney et al., "Photodynamic Therapy of Cancer", Comprehensive Therapy, 14, No. 5, 43–55, May 1988.

Fairchild et al., "In Vitro Determination of Uptake, Retention, Distribution, Biological Efficacy, and Toxicity of Boronated Compounds for Neutron Capture Therapy", Cancer Research, 50, 4860–4865, Aug. 15, 1990.

Fairchild et al., "Optimization of Boron and Neutron Delivery for Neutron Capture Therapy", Pigment Cell Research, 2, 309–318, 1989.

Finkel et al., "Distribution of $^{10}$B After Infusion of Na$_2$ $^{10}$B$_{12}$H$_{11}$SH Into A Patient with Malignant Astrocytoma: Implications for Boron Neutron Capture Therapy", Neurosurgery, 24, No. 1, 6–11, Jan. 1989.

Hawthorne et al., "Preparation of Tumor–Specific Boron Compounds. 1. In Vitro Studies Using Boron–Labeled Antibodies and Elemental Boron as Neutron Targets" Journal of Medicinal Chemistry, 15, No. 5, 449–452, May 1972.

Joel et al., "Pharmacokinetics and Tissue Distribution of the Sulfhydryl Boranes (Monomer and Dimer) in Glioma–Bearing Rats", Strahlenther. Onkol., 165, 167–170, 1989.

Kahl et al., "New Tumor Localizers: Advances in the Use of Low Density Lipoproteins (LDL)" Strahlenther Onkol., 165, 137–139, 1989.

Mishima et al., "Treatment of Malignant Melanoma by Single Thermal Neutron Capture Therapy with Melanoma–Seeking $^{10}$B–Compound", The Lancet, 388–389, Aug. 12, 1989.

Miura et al., "Preparation of Carboranyl Porphyrins for Boron Neutron Capture Therapy", Tetrahedron Letters, 31, No. 16, 2247–2250, 1990.

Sneath et al., "Protein–Binding Polyhedral Boranes.1" Journal of Medicinal Chemistry, 17, No. 8, 796–799, 1974.

Wong et al., "Boron Hydride Derivatives for Neutron Capture Therapy.1", Journal of Medicinal Chemistry, 17, No. 8, 785–791, Aug. 1974.

Fairchild et al., "A Comparison of Particle Radiation Therapy Modalities", Chpt. 2 in Boron–Neutron Capture Therapy for Tumors, H. Hatanaka, editor, Nishimura, 1986.Hatanaka, "Clinical Experience of Boron–Neutron Capture Therapy for Gliomas"—A Comparison with Conventional Chemo–Immuno–Radiotherapy, Chpt. 25 in Boron–Neutron Capture Therapy for Tumors, H. Hatanaka, editor, Nishimura, 1986.

(List continued on next page.)

Primary Examiner—Chhaya D. Sayala
Attorney, Agent, or Firm—Majestic, Parsons, Siebert & Hsue

[57] ABSTRACT

Carborane substituted porphyrin compounds complexed with a metal or transition metal have a variety of therapeutic uses. These compounds have been found, for example, selectively to inhibit viral aspartyl proteases. The transition metal complexes are useful both therapeutically in BNCT (boron neutron capture therapy) as well as for MR contrast enhancement. Particularly preferred compounds in accordance with the invention use the dipotassium salt of 2,4-bis-[α,β-(1,2-dicarbaclosododecaborane carboxy)ethyl] deuteroporphyrin, which is complexed with a metal or a transition metal. These compounds are well solubilized in water, and are suitable for oral administration.

8 Claims, 2 Drawing Sheets

OTHER PUBLICATIONS

Gawronski et al., "Exciton Effects in Chiral Planar 1,3–Dienes and α,β–Unsaturated Carbonyl Compounds. Configurational Application", *J. Am. Chem. Soc.*, 109 (1987) pp. 6726–6730.

Des Jarlais et al., "Structure–Based Design of Non–Peptide Inhibitors Specific for the Human Immunodeficiency Virus I Protease," *Proc. Natl. Acad. Sci. USA*, 87, (1990), pp. 6644–6648.

Ashorn et al., "An Inhibitor of the Protease Blocks Maturation of Human and Simian Immunodeficiency Viruses and Spread of Infection," *Proc. Natl. Acad. Sci. USA*, 87, (1990), pp. 7472–7476.

Baum, "Progress Fitful on Understanding AIDS, Developing Therapies," *C&EN*, 70:34 (Aug. 24, 1992), pp. 26–31.

Pauwels et al., "Potent and Selective Inhibition of HIV–1 Replication in vitro by a Novel Series of TIBO Derivatives," *Nature*, 343 (Feb. 1, 1990), pp. 470–474.

Larder and Kemp, "Multiple Mutations in HIV–1 Reverse Transcriptase Confer High–Level Resistance to Zidovudine (AZT)," *Science*, 246 (Dec. 1, 1989), pp. 1155–1158.

Huang et al., "Boronated Metalloporphyrins: A Novel Approach to the Diagnosis and Treatment of Cancer Using Contrast–Enhanced MR Imaging and Neutron Capture Therapy," *JMRI*, 3(2), (Mar./Apr. 1993), pp. 351–356.

Chen et al., "Paramagnetic Metalloporphyrins as Potential Contrast Agents in NMR Imaging," *FEBS Lett.*, 168 (1984), pp. 70–74.

Ogan et al., "Metalloporphyrin Contrast Enhancement of Tumors in Magnetic Resonance Imaging: A Study of Human Carcinoma, Lymphoma, and Fibrosarcoma in Mice," *Invest. Radiol.*, 22 (1987) pp. 822–828.

Fiel et al., "A Comparative Study of Manganese Meso–S-ulfonatophenyl Porphyrins: Contrast–Enhancing Agents for Tumors," *Magn. Reson. Imaging*, 8 (1990), pp. 255–259.

Furmanski et al., "Metalloporphyrin Enhancement of Magnetic Resonance Imaging of Human Tumor Xenografts in Nude Mice," *Cancer Res.*, 48 (1988), pp. 4604–4610.

Bockhorst et al., "Proton Relaxation Enhancement in Experimental Brain Tumors: In vivo NMR Study of Mn(III) TPPS in Rat Brain Gliomas," *Magn. Reson. Imaging*, 8 (1990), pp. 499–504.

Lyon et al., "Tissue Distribution and Stability of Metalloporphyrin MRI Contrast Agents," *Magn. Reson. Med.*, 4 (1987), pp. 24–33.

Fiel et al., "Mechanism of the Localization of Manganese (III) Mesotetra (4–sulfonatetephenyl) Porphine in Mice Bearing L1210 Tumors," *Cancer Lett.*, 40 (1988), pp. 23–32.

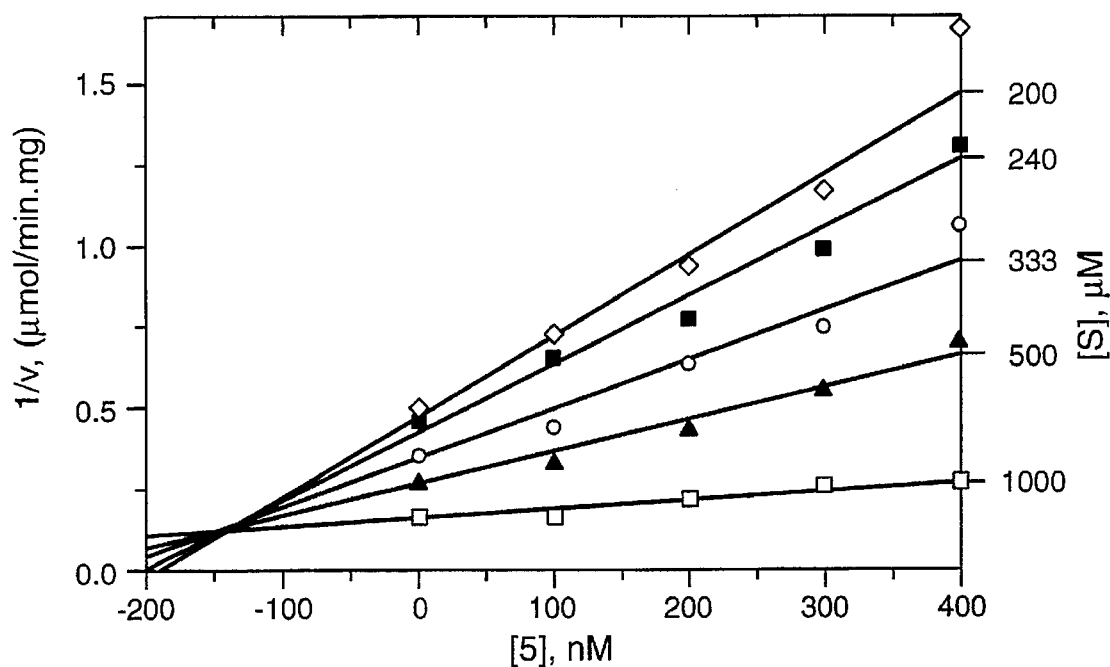
FIG._1A
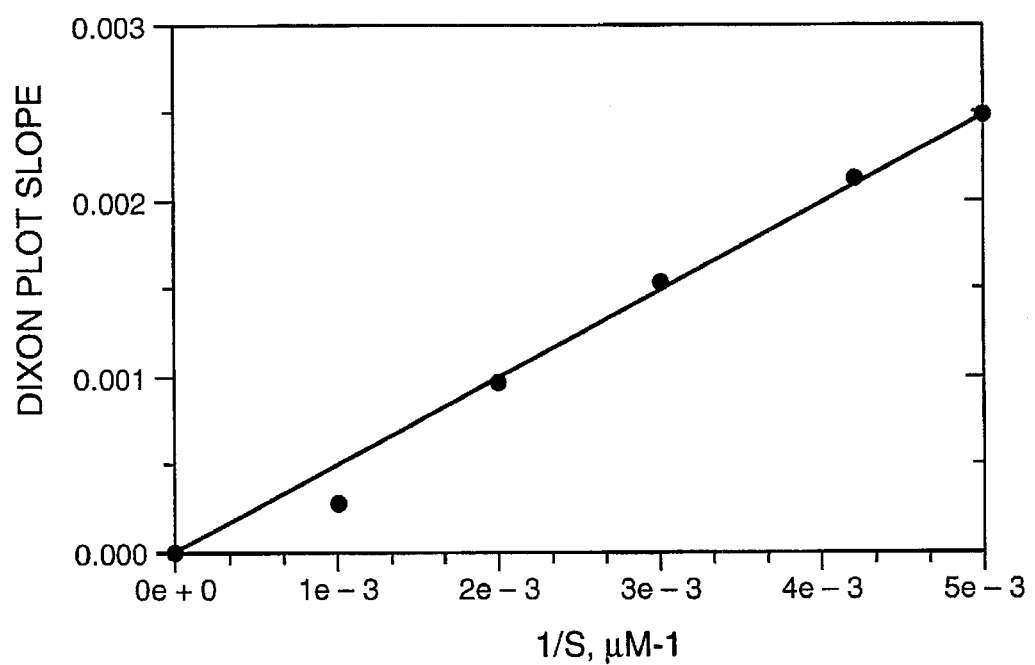
FIG._1B

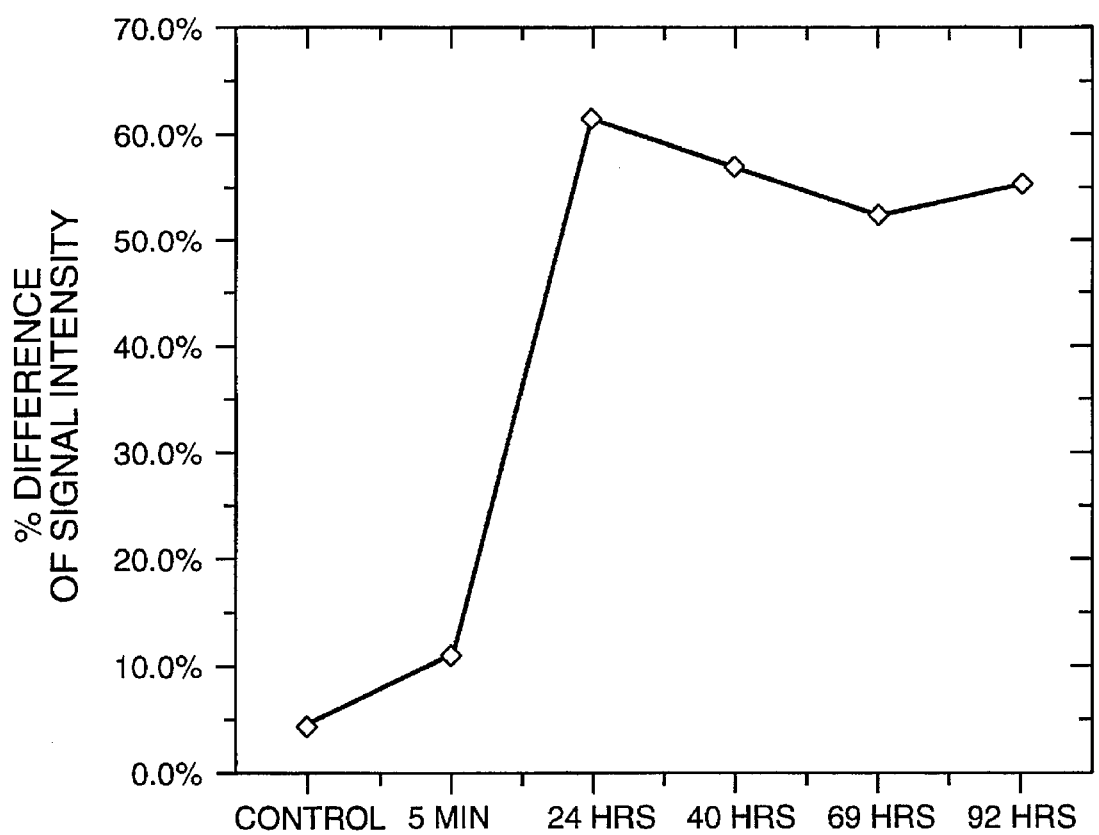
FIG._2

BORONATED METALLOPORPHYRINE AND THERAPEUTIC METHODS

This is a continuation of application Ser. No. 08/130,302, filed Oct. 1, 1993, which is a continuation in part of Ser. No. 07/940,095, filed Sep. 3, 1992 (both now abandoned), and of U.S. Ser. No. 07/869,611, filed Apr. 16, 1992 now U.S. Pat. No. 5,284,831, issued Feb. 8, 1994), the former being a continuation in part and the latter being a divisional of U.S. Ser. No. 07/616,679, filed Nov. 21, 1990, now U.S. Pat. No. 5,149,801, issued Sep. 22, 1992, all of common assignment herewith.

This invention was made with Government support under Grant Nos. CA-37961 awarded by the National Institutes of Health. The Government has certain rights in this invention.

FIELD OF THE INVENTION

The present invention generally relates to therapeutic uses of porphyrins, and more particularly to metal complexes of porphyrins with hydrophobic glycol derivative substituents at pyrrole ring positions 2 and 4.

BACKGROUND OF THE INVENTION

U.S. Pat. No. 4,959,356, issued Sep. 25, 1990, inventors Miura and Gabel describe boronated porphyrin compounds for use in boron neutron capture theory (BNCT). Similar compounds are discussed in an article by Miura et al. *Tetrahedron Letters*, Vol. 31, No. 16, pp. 2247–2250 (1990). The boronated porphyrins described by Miura have vinyl carborane moieties and are reported to be water insoluble. Thus the borane cages must be opened to obtain water solubility. But by opening those borane cages, one encounters significantly more toxicity for the compounds. Moreover, the resultant open-cage compounds are still not sufficiently water soluble to enable administration without the use of adjuvant substances (e.g., polyethylene glycol). Also the compounds which Miura et al. describe are (at most) 19% boron by weight in the physiologically useful ($K^+$-salt) form. This is a disadvantage since limiting human doses may well be determined by the amount of porphyrin unit doses which may be tolerated.

In addition to neutron capture therapy (NCT) generally and boron neutron capture therapy (BNCT) more specifically, additional uses of porphyrins in cancer therapies are those therapeutic strategies generally referred to as photodynamic therapy (PDT). A review article by Delaney and Glatstein in *Comprehensive Therapy*, pp. 43–55 (May 1988) describes this therapeutic strategy where a light-activated photosynthesizer can interact with ground state molecular oxygen to yield reactive oxygen species (via singlet oxygen). Since porphyrins of many structural types localize in a wide variety of malignant tumors, this localization has formed the basis for treatment of at least 3000 patients in the United States alone (twice that worldwide) over the past several years through PDT. Complete response (disappearance of tumor or biopsy proven) has occurred in a high percentage of patients in relatively advanced stages of skin, bladder, and lung cancers, and cancers of the reproductive system through photodynamic therapy.

U.S. Pat. No. 5,109,016, issued Apr. 28, 1992, inventors Dixon et al., describes compositions said to inhibit replication of human immunodeficiency virus by porphyrin and certain porphyrin-like compounds. These compounds were tested for inhibition of reverse transcriptase as a screening method to determine inhibition of HIV; however, during the 8th International Conference on AIDS, held in late July, 1992, in Amsterdam, some presentations suggested that many drugs that showed initial promise against HIV-1 have been found to have serious shortcomings because HIV-1 rapidly becomes resistant to the so-called "non-nucleoside reverse transcriptase inhibitors." See, *C&EN*, 70:34, pp. 26–31 (Aug. 24, 1992). As an example of a non-nucleoside derivative that binds to a site other than the active site (non-competitive inhibition), see Pauwels et al., *Nature*, 343, pp. 470–474 (1990); however, resistance develops rapidly to this derivative.

SUMMARY OF THE INVENTION

In one aspect of the present invention, a metallo-complexed porphyrin compound in accordance with this invention preferably has the structure

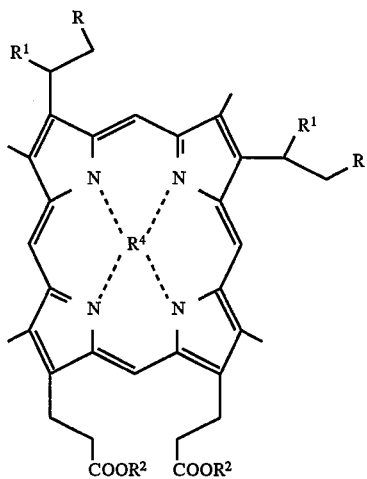

where each of R and $R^1$ is selected from —H, —OH, or

and at least one of R and $R^1$ is

$R^3$ preferably is a carborane, $R^2$ is —H, an alkyl, or an aryl, having 1 to about 7 carbon atoms, or a physiologically acceptable salt, and $R^4$ is a metal or a transition metal.

Particularly preferred as the porphyrin compound for practice of various therapeutic applications is the manganese chelate of the tetrakiscarborane carboxylate ester of 2,4-(α,β-dihydroxylethyl)deutero-porphyrin IX. This particularly preferred porphyrin compound has at least a 60-fold greater affinity for HIV-1 protease than for cellular aspartyl proteases, can enhance magnetic resonance imaging (MRI) contrast between tumor and normal tissue, and has been tolerated in mice at doses as high as 100 mg/kg.

In another aspect of the present invention, compounds such as illustrated above, or without the $R^4$ metal or transition metal, are useful in treating patients with a malignant tumor in boron-neutron capture theory (BNCT) or in photodynamic therapy (PDT). However, the transition metal complexes are additionally useful for tumor enhancement and thus have dual functions of diagnosis as well as therapy.

BRIEF DESCRIPTION OF THE DRAWINGS

FIG. 1 is a Dixon plot of inhibition by one inventive embodiment with an inhibition constant (Ki) of 140±25 nM, which is consistent with a competitive mode of inhibition and shows the strength of binding to the protease; and FIG. 2 graphically illustrates the percent difference of MRI signal intensity between tumor and normal brain tissue before and after administration of a particularly preferred embodiment of the invention.

DETAILED DESCRIPTION OF THE PREFERRED EMBODIMENTS

Broadly, the invention relates to compositions and therapeutic compositions and uses where the drug being used can be viewed as consisting of or built from a porphine precursor, whose basic structure is illustrated as Formula P:

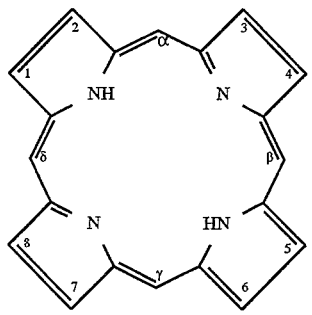

FORMULA P

Porphine, of course, is the parent (or core) substance of the porphyrins, which have side chains and alkyl groups substituted for some hydrogens in the porphine pyrrole rings. Compounds of the invention preferably have substituents on at least two of the pyrrole rings of porphine at pyrrole ring positions 2 and 4. At least some of these substituents at pyrrole ring positions 2 and 4 preferably are hydrophobic derivatives of glycol.

Preferred embodiments of the invention have the structure illustrated by Formula 1:

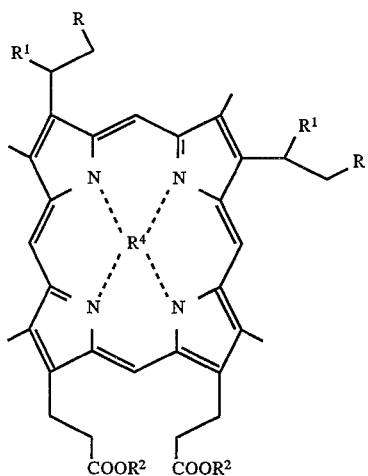

FORMULA 1 where each of R and R$^1$ is selected from —H, —OH, or

—OCR$^3$ and at least one of R and R$^1$ is

—OCR$^3$,

R$^3$ is a carborane or a substituted or unsubstituted phenyl (with substituents such as nitro, hydroxyl, amino, halo, or nitrile), substituted or unsubstituted naphthyl (with substituents such as described for phenyl), or other hydrophobic groups, such as bulky alkyls or aryl groups, R$^2$ is —H, an alkyl, or an aryl, having 1 to about 7 carbon atoms, or a physiologically acceptable salt, and (when present) R$^4$ is a metal or a transition metal.

Particularly preferred embodiments of this invention are where R$^3$ is a carborane, and most preferred are closo-carboranes, and R$^4$ is metal ion (e.g. Zn(II)), or a transition metal, such as Mn(III), cu(II), or co(II).

The presence of the R$^4$ metal assists in stabilizing the molecules against, for example, sensitivity to light. The presence of the R$^4$ transition metal, particularly manganese, provides a dual function for the molecule: as a contrast agent for MR imaging as well as a therapeutic agent for BNCT. The former is important because conventional manipulation of pulse sequences frequently does not provide clear differentiation between tumor and normal tissue in MR imaging. Most contrast agents currently under investigation do not localize specifically and selectively in tumors, but rather remain solubilized in blood or in extra vascular compartments.

Thus, particularly preferred metalloporphyrins of this invention can be used to provide a single agent with therapeutic potential having enhanced diagnostic capability of MR imaging as a new approach for cancer treatment, in addition to their therapeutic uses in BNCT, PDT, and others.

Therapeutic formulations may be prepared having the desired degree of purity with the optional physiologically acceptable carriers, excipients or stabilizers. Acceptable carriers, excipients or stabilizers are nontoxic to recipients at the dosages and concentrations employed when administered, and include buffers such as phosphate, citrate, and other organic acids; anti-oxidants including ascorbic acid; low molecular weight (less than about 10 residues) polypeptides; proteins, such as serum albumin, gelatin or immunoglobulins. Other components can include glycine, blutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or PEG.

For example, in using embodiments of the invention for neutron capture therapy, it is believed that the desired isotope may be administered so as to accumulate in the tumor in amounts potentially as low as about 1 µg of $^{10}$B isotope per gram tissue (equivalent to 1 ppm). To accumulate the desired amount of isotope in the tumor, compounds of the invention are generally administered by injecting patients with a dose of about 100 mg/kg body wt. of the compound in a pharmaceutically acceptable medium or carrier, as well known to the art, prior to subjecting the patient to the neutron beam. As will be understood, the amount of compound in accordance with the invention that one desires to accumulate in the tumor will depend upon the amount of boron-10 present in the compound (with compounds enriched to about 95% over the naturally occurring about 20% of $^{10}$boron being preferred) and with the neutron beam power used. While i.v. administration is preferred, i.p.

administration can be used, and it is believed that the inventive embodiments are suitable for oral administration. One can give the total to be administered as a single bolus of 100 mg/kg or in serial portions totalling about 100 mg/kg over a period of about 7 to 10 days.

We believe that administrating as little as 10 mg/kg body weight of the embodiments may produce sufficiently high tumor porphyrin levels to be efficacious in photodynamic therapies.

Conjugates, or complexes, of inventive embodiments with lipoprotein are also useful and can be simply prepared for delivery of an embodiment using low density lipoprotein as the carrier agent, either of two methods of complexation are preferred. For the first, human low density lipoprotein, isolated from fresh human plasma by preparative density gradient ultracentrifugation, is treated by the method described by Kahl and Callaway, *Strahlenther Onkol.* 165:137 (1989), incorporated by reference. In brief, this method involves removal of the native cholesterol ester core of LDL by a published procedure, Krieger et al., *Biol. Chem.*, 259:3845 (1979), also incorporated by reference, incubation of the delipidated LDL with a solution of BOPP-dimethyl ester in $CCl_4$ (6 mg/200 µL), removal of the $CCl_4$ by nitrogen flow, and solubilization of the reconstituted LDL in 10 mM tricine (Ph 8.6). This procedure results in LDL particles containing approximately 300 molecules of BOPP-dimethyl ester per LDL particle. LDL reconstituted in this manner behaves in a fashion similar to native LDL and enters cells by receptor-mediated endocytosis.

A second method is simpler, but results in fewer molecules of the sensitizer per LDL particle. Human plasma is incubated at 37° C. with an aqueous solution of BOPP (in the potassium salt form; 4 µM) for 30 minutes. The plasma lipoprotein fractions are then separated by density gradient ultracentrifugation. Approximately 25% of the administered porphyrin is found bound to the LDL fraction, 20% to the VLDL, and 55% to the HDL fraction.

The BOPP embodiment in BNCT uses $^{10}B$-enriched carborane. As this material is presently unavailable from commercial sources, it must be made from $^{10}B$-enriched $B_{10}H_{14}$. Preparations are taught in U.S. Pat. No. 5,149,801, incorporated by reference.

The embodiments, in addition to utility in methods of treating a patient with a malignant tumor through BNCT (for example, by administering to the patient a tumor-concentrating dose and then activating the inventive embodiment with neutrons to cause alpha particle emission) are also useful in PDT when sufficient photons (such as from a source that emits red light, to convert ground state molecular oxygen to singlet oxygen) irradiate the patient's tumor.

Other biomedical applications for compounds in accordance with the invention include diagnostic or therapeutic uses, such as for atherosclerosis. This is because nonboronated porphyrins with physical and chemical properties similar to compounds of the invention have been found to localize in plaques of atherosclerosis patients. Once taken up by the plaques, methods such as laser angioplasty can be used to localize and diagnose the plaque areas through use of appropriate wavelengths of light.

Compounds with boron cage systems in which one or more carbon atom is present as an integral part of an electron-delocalized boron framework are given the general name "carboranes," which term includes both closed polyhedra and open-cage structures. Carboranes are distinct from other organoboron species, such as the alkyl boranes, because the carbon(s) are part of the cage itself rather than present as a ligand. An early monograph on these electron-deficient boron cage compounds is by Grimes, *Carboranes,* Academic Press (1970), which describes nomenclature, structure, synthesis, and properties of carboranes, including those of interest for this invention. There are a series of stable 12-atom polyhedral boron cage systems that have been isolated in at least three isomeric forms. Two particularly preferred cage system isomers for this invention are the 1,2-$C_2B_{10}H_{12}$ isomer and the 1,7-$C_2B_{10}H_{12}$ isomer (the latter sometimes represented as "$HCB_{10}H_{10}CH$").

Particularly preferred for embodiments of the invention are wherein $R^3$ is a closo-carborane, and most particularly is the 1,2-icosahedral isomer or 1,7-icosahedral isomer, whether substituted or unsubstituted. An illustrative substituent is, for example, a carboxyl group, which may be desirable to aid in solubilizing the porphyrin compound. The physical properties of the 1,2-icosahedral isomer and the 1,7-icosahedral isomer are similar.

The closo-carboranes are particularly preferred because the open-cage carboranes lead to significantly increased toxicity of what can otherwise be substantially non-toxic compounds. Closed-cage and open-cage systems are typically designated by the prefixes "closo-" and "nido-," respectively.

Conversion of the bis-glycol substituents to tetra-ester is surprising due to the size and steric hindrance considerations for preferred moieties. Where one desires to only obtain a di-ester carborane (such as with an $R^1$ at each of the 2 and 4 porphyrin ring positions as hydroxyl or hydrogen), then typical acylation agents, such as pyridine or trimethylamine can be used; however, where one desires the tetra-ester, such as in preparing a particularly preferred embodiment we have coined as "BOPP," then the conversion of bis-glycol critically depends upon the use of p-dimethylaminopyridine (DMAP) as a hyper-acylation reagent.

The BOPP embodiment is especially useful where a stable, quite water soluble, substantially non-toxic compound with a large number of boron atoms (40) is desired. The large number of boron atoms is believed useful, for example, in treating solid tumors with neutron capture therapy (NCT). In the potassium salt form, the BOPP embodiment is very water soluble and can be readily prepared in concentrations of at least about 100–200 mg/mL, yet the compound retains a high degree of lipophilicity. We also have designated this BOPP embodiment by the phrase "tetra-carborane carboxylate ester of 2,4-Di($\alpha,\beta$-dihydroxyethyl)deuteroporphyrin (IX)" or by "embodiment 1."

This embodiment 1 can be used, for example, to inhibit retroviral aspartyl proteases in vitro. Although removal of all four carborane moieties substantially reduces inhibition of aspartyl proteases, we have found that removal of only two of the four carborane cages has little effect on binding with the HIV-1 and HIV-2 proteases. This suggests that only two of the four closo-carborane cages are responsible for most of the binding interaction. The metacarborane isomer binds approximately 60-fold less tightly, indicating that not only the presence of the carborane groups but also their isomeric conformation is important. Adding a methyl group to the unsubstituted carborane cage CH also substantially decreases the binding affinity.

The carborane cages appear to have a specific interaction with the HIV proteases, which results in high affinity between the molecule and enzymes. Replacement of the carborane cages with similarly sized, but less hydrophobic groups, such as benzoyl, adamantoyl, or even β-naphthoyl groups gives inhibitors with $IC_{50}$ values in the low micromolar range.

As earlier noted, the inventive porphyrin molecules tend to have sensitivity to light, but can be stabilized by forming transition metal complexes. Although complexation with Co(II) or Cu(II) weakens binding about 10-fold, addition of Mn(III) has only a two-fold effect on inhibition, which indicates that the hexacoordinate Mn(III) may be able to make favorable ionic interactions with the enzyme.

While oral administration is preferred for compounds of the invention, i.v. or i.p. administration can be used. The preferred BOPP dipotassium salt ester embodiment is substantially water soluble and is thus suitable for oral administration. One can administer as a single portion, such as of 100 mg/kg, or administer in serial portions over a period of time as advised by an attending physician. The particularly preferred embodiment has been given to mice at doses as high as 200 mg/kg with no apparent signs of morbidity or mortality. Mice receiving this embodiment at 100 mg/kg by i.v. bolus have been exposed to peak plasma concentrations of almost 1 mM. This is well above the concentrations that are effective for in vitro anti-proteoyl activity or ex vivo anti-viral activity. Thus, toxicity does not appear to be an impediment for practice of the invention. Yet further, when we performed experiments to determine specificity, we found that the particularly preferred embodiment was much more specific for HIV-1, HIV-2, and the simian retrovirus, SIV aspartyl proteases, than to the cellular aspartyl proteases such as renin and pepsin.

Porphyrin compositions used as described in accordance with this invention are substantially bio-available. As will be exemplified hereinafter, in vitro effect of the various porphyrin derivatives on HIV-1 and HIV-2 protease activity was examined by monitoring the cleavage of a decapeptide substrate. Since many of the derivatives tested were insoluble in buffer alone at the concentrations necessary for the $IC_{50}$ determinations, 5% DMSO was used to increase solubility and to allow a fair comparison of the binding affinities of the various compounds. However, preferred embodiments in accordance with this invention when used as inhibitors are soluble in aqueous solution, and these preferred embodiments were actually more potent when assayed in the absence of DMSO.

Aspects of the invention will now be exemplified by the following examples, which are understood to be illustrative and not limiting.

EXAMPLE 1

Synthesis of bis-glycol porphyrin dimethyl ester

Dried protoporphyrin dimethyl ester (4.4 g) was dissolved in 1.6 L of dioxane and 3.0 mL of pyridine in the dark. This solution was thoroughly bubbled with argon to remove oxygen. Osmium tetroxide (4.0 g) was dissolved in 200 ml argon-degassed diethyl ether and added to the dioxane-porphyrin solution. The solution was well stirred under Ar in the dark for 24 hours. Sodium sulfite (8.8 g) was dissolved in 160 mL distilled, argon-degassed water and added to the solution. The reaction was heated to 75° C. on a steam bath for 6 hours. The reaction solution was cooled to 53°–55° C. and filtered quickly through a 1.5 L medium fritted funnel and washed with a small portion of dioxane. Filtrate was evaporated in vacuo and then 200 mL and 750 mL of water was added with stirring to crystallize the product. The crystals were filtered through a 1.5 L medium fritted funnel and washed with 100 mL water. The filtered solid was suspended in 200 mL, 15% methanol/methylene chloride and 450 mL hexane added with stirring to complete crystallization. The procedure was repeated to remove impurities if necessary.

EXAMPLE 2

Synthesis of 2,4-bis-[α,β-(2-dicarbaclosododecaborane carboxy)ethyl] deuteroporphyrin (IX) dimethyl Carborane carboxylic acid was synthesized from 1,2-$B_{10}C_2H_{12}$ by the method of Zakharkin et al., Akad. Nauk SSSR, Ser. Khim., p. 1376 (1967) and Zakharkin et al., Tet. Lett., p. 1147 (1964), incorporated by reference. Briefly, this method involves treatment of the o-carborane with one equivalent of n-butyl-lithium in benzene to produce the mono-lithio compound. This species is reacted with $CO_2$ to give the lithium salt of the carboxylate which gives the free carboxylic acid on acidification. Conversion to the acid chloride is also by the method of Zakharkin et al. using $PCl_5$ in toluene. Vacuum distillation of the reaction mixture gives the carborane carbonyl chloride.

The bis-glycol porphyrin prepared as described by Example 1 (500 mg, 0.75 mmol) was dissolved in dry methylene chloride (200 mL), and the solution bubbled with argon. To the above solution o-carboranyl acid chloride (690 mg, 3.341 mmol) was added. The solution was stirred, and 4-dimethyl aminopyridine (DMAP) 371 mg, 3 mmol) was added to the solution. The solution was stirred at room temperature for one hour and poured into water. The organic layer was separated, washed with dilute hydrochloric acid three times, saturated sodium bicarbonate (3×), water (2×), and dried over sodium sulfate. Unreacted carborane carboxylic acid was removed from the bicarbonate washes by acidification and extraction with hexane or diethyl ether. The solution was filtered and evaporated in vacuo to yield a crude product. Three spots were obtained on analytical TLC plate by developing with 100% methylene chloride. The top spot is the tetracarboranyl porphyrin dimethyl ester, and the two slower spots are tri- and di- carborane esters, respectively. The tetracarboranyl porphyrin dimethyl ester was separated by filtering the methylene chloride solution of the crude products through a silica gel pad. The first mobile band was obtained by washing with 100% methylene chloride (110 mL) and evaporating to dryness. Crystallization from methylene chloride-hexane gave 849 mg. Isolated yield was 80–85%. We coined "BOPP" as a shorthand designation for the inventive embodiment whose preparation has just been described (in the dimethyl ester form).

The conversion of bis-glycol to tetra-ester critically depends upon the use of p-dimethylaminopyridine (DMAP) as a hyper-acylation reagent and upon its stoichiometric relationship with bis-glycol and acid chloride. The rate of formation of tetra-ester product in the absence of nitrogen base is extremely slow, if it occurs at all. We have found that when pyridine or trimethylamine (two other frequently used acylation agents) were used rather than the DMAP reagent, then the rate of tetra-ester formation was very slow when compared to use of DMAP. However, when one wishes to prepare the diester form rather than the tetra-ester, then these other acylation agents (such as TEA) should be used rather than DMAP.

EXAMPLE 3

Synthesis of 2,4-bis-[α,β-(1,2-dicarbaclosododecaborane carboxy)ethyl] deuteroporphyrin (IX)

To a solution of the tetracarboranylporphyrin dimethyl ester prepared as described in Example 2 (300 mg, 0.224 mmol) in 100 mL ether was added 25% hydrochloric acid (100 mL). The solution was stirred at room temperature overnight. The solution was washed with copious water (to dilute acid). The ether layer was separated, dried over sodium sulfate and evaporated in vacuo to give the tetracarboranyl porphyrin diacid inventive embodiment we designate in shorthand as "BOPP free acid." Quantitative yield.

EXAMPLE 4A

Synthesis of 2,4-bis-[α,β-(1,2-dicarbaclosododecaborane carboxy)ethyl] deuteroporphyrin dipotassium salt (IX)

The tetracarboranyl porphyrin diacid, or "BOPP free acid" prepared as described in Example 3, (150 mg) was dissolved in 20 mL THF and 15 mL water was added. The solution was passed through 1×10 cm cation exchange resin, 200–400 dry mesh. The eluate was evaporated to increase the ratio of water (up to 60/40 water/THF) and passed through ion exchange resin again. The final eluate was evaporated to dryness in vacuo. The resulting dipotassium salt is well solubilized in water. We designated this inventive embodiment as "BOPP." We now prefer using acetone instead of THF.

EXAMPLE 4B

Synthesis of 1,7 Isomer

The 1,7 closo-carborane isomer of BOPP was prepared in the same manner using 1,7-carborane carbonyl chloride, but with the following difference. Thermal isomerization of the 1,2-carborane to the 1,7-carborane occurs at 450°–500° C. See Grafstein and Dvorak, *Inorganic Chemistry*, 2:1128 (1963). Yields in this process approach 95% when a flow through a pyrolysis system is used in conjunction with an inert carrier gas. This approach is preferred for the conversion of $^{10}$B-enriched 1,2 isomer to the 1,7 isomer.

Other sterically hindered organic acid chlorides were used to incorporate desired $R^3$ moieties in an analogous manner to Examples 1–4A. Characterization in all cases was by mass spectrometry, proton magnetic resonance, and UV-visible spectroscopy.

EXAMPLE 5

Evidence in support of the structures prepared in Examples 2–4A came from mass spectrometric and spectroscopic sources. The LSIMS mass spectrum of BOPP-dimethyl ester in a tetraethylene glycol matrix shows a molecular ion cluster ($MH^+$) at nominal mass 1341 corresponding to the formula $C_{48}H_{83}B_{40}N_4O_{12}$. The shape of the theoretical molecular ion cluster of this formula is nearly identical to the 15-peak ion cluster observed at 1341. Similarly, LSIMS of the BOPP free acid produces a molecular ion cluster at nominal mass 1321 corresponding to the formula $C_{46}H_{79}B_{40}N_4O_{12}$ and whose shape is almost identical to the theoretical molecular ion cluster. In both mass spectra, four successive losses of $B_{10}H_{11}C_3O_2$ fragments are observed corresponding to loss of the carborane carboxylate. The visible spectrum of BOPP-dimethyl ester in $CH_2Cl_2$ (10 μM) consists of peaks at 404 (Soret) 502, 536, 572, and 624 nm.

A summary of the 300 MHz proton N.M.R. data for BOPP-dimethyl ester is presented in Table 1.

TABLE 1*

| δ | multiplicity | assignments |
|---|---|---|
| 10.27, 10.23, 10.16, 10.14 | s, 4H | meso H |
| 7.68 | m, 2H | α CH |
| 5.68; 4.99 | m, 4H | β $CH_2$ |
| 4.41 | m, 4H | Por-$CH_2$ |
| 4.17; 4.10 | s, 4H | carborane CH |
| 3.81; 3.80 | S, 6H | $CO_2CH_3$ |
| 3.68; 3.64 3.63; 3.61 | S, 12H | β-$CH_3$ |
| 3.30 | m, 4H | —$CH_2CO_2R$ |
| −3.65 | s, 2H | NH |

*N.M.R. spectrum was recorded in $CDCl_3$ (ca. $5 \times 10^{-3}$ M) at 300 MHz at ambient temperature with TMS internal reference.

The lack of a molecular $C_2$ axis is clearly demonstrated by the presence of four, distinct resonances for the meso-H and β-$CH_3$ groups. This makes difficult a detailed analysis of the spectrum, especially the conformation of the carboranyl ester-bearing side chains. Nevertheless, several features are apparent. At least two distinct and equivalent carborane CH environments are present, perhaps a reflection of the primary and secondary alcohol ester functions. Three resonances are assigned to the two-carbon side chain protons, a chiral methine ($H_α$), and pro-chiral methylene ($H_β$). The $H_α$ assigned to 7.68 ppm is strongly deshielded by virtue of its being bound to a carbon bearing two strongly deshielding group: the porphyrin (ring current) and carboranyl acyl (σ effects). The two $H_β$ resonances have significant (0.7 ppm) chemical shift differences which might arise if the most stable configuration forces one of the $H_β$ protons into a position over the porphyrin ring when it is subject to ring current deshielding relative to the other.

There are three possible configurations for the groups bound to the ethyl side chain, two gauche and one anti. Computer modeling based on the crystal structure of mesoporphyrin IX dimethyl ester suggests that the anti-configuration should offer the least amount of steric hindrance for all functional groups. The α-carborane ester points down at an angle of about 45° and away from the porphyrin while the β-ester points up and over the porphyrin. This configuration also places one of the pro-chiral $H_β$ protons in a pocket formed by the porphyrin plane, a meso-H and the $O_α$, giving rise to its potential deshielding relative to the other $H_β$. However, one gauche configuration also provides some side chain flexibility and deshielding of one $H_β$ from a similar pocket. In the remaining gauche form, all J-J coupling constants should be large and modeling indicates significant steric hindrance for the $O_β$.

EXAMPLE 6A

In a manner analogous to that described by the just described examples, a number of inventive embodiments and a comparative compound were prepared where Table 2 gives the R, $R^1$, and $R^4$ moieties.

TABLE 2

| Inventive Embodiment | R | $R^1$ | $R^4$ |
|---|---|---|---|
| 1 | $OCOB_{10}H_{11}C_2$ | Same as R | $H_2$ |
| 2 | H | $OCOB_{10}H_{11}C_2$ | $H_2$ |
| 3 | $OCOB_{10}H_{11}C_2$ | Same as R | Mn(III) |
| 4 | $OCOB_{10}H_{14}C_3$ | " | $H_2$ |
| 5 | $OCOB_{10}H_{11}C_2$ | " | Cu(II) |
| 6 | $OCOB_{10}H_{11}C_2$ | " | Co(II) |

TABLE 2-continued

| Inventive Embodiment | R | R$^1$ | R$^4$ |
|---|---|---|---|
| 7 | OCO(adamantoyl) | " | H$_2$ |
| 8 | OROp-[(CH$_3$)$_2$N]benzoyl | " | H$_2$ |
| 9 | meta-OCOB$_{10}$H$_{11}$C$_2$ | " | H$_2$ |
| 10 | OCOC$_6$H$_5$ | " | H$_2$ |
| 11 | OCO(β-naphthoyl) | " | H$_2$ |
| Comparative | | | |
| 12 | OH | OH | H$_2$ |

Compound 2 was prepared in the dimethyl ester form as described by Example 2 and converted to the free acid as by Example 3.

Compounds 3, 5, and 6 are metalloporphyrin derivatives of BOPP prepared by the general procedure outlined below (and also exemplified in Example 6B).

BOPP dimethyl ester (130 mg/0.099 mmol) was dissolved in glacial acetic acid (9 ml) and pulverized anhydrous manganese (II) acetate (50 mg; 0.289 mmol) was added. The vessel was loosely stoppered and the solution stirred in the dark at 20° C. The course of reaction was followed spectrophotometrically by observing the disappearance of the red fluorescence characteristic of free base porphyrin. When all traces of this red fluorescence had disappeared (20 h), ether (125 ml) was added to the solution. The ether solution was washed with an equal volume of water (3×), dried over sodium sulfate, and evaporated in vacuo. The solid product was redissolved in ether (30 ml) and 25% aqueous HCl (30 ml) added. After stirring overnight at 20° C., the mixture was poured into ether (200 ml) and washed four times with water (500 ml). The ether layer was again dried, filtered, and evaporated in vacuo to yield pure product (166 mg, 75.1% yield).

The water soluble Mn(III) porphyrin dipotassium salt is estimated to contain 5% water by weight. The absorption spectrum of this compound showed no evidence of free-base porphyrin and consisted of peaks at 368 nm (log ε=4.82), 418 nm (sh) (4.36), 460 nm (4.60), 546 nm (3.98), and 579 nm (sh) (3.82). The Cu(II) (compound 5) and Co(II) (compound 6) derivatives were prepared in a similar fashion to 3 using the appropriate metal salt. Their UV-Vis absorption spectra were similar to that of compound 3 and were characteristic of metalloporphyrins of the hematoporphyrin class. As with 3, no evidence of unmetallated free base porphyrin was observed in the UV-Vis spectra.

EXAMPLE 6B

A preparation of Mn-BOPP was used in the tumor enhancement studies reported in Example 8. To 335 mg (0.254 mmol) of the tetracarboranyl porphyrin diacid (BOPP diacid) dissolved in 20 mL of glacial acetic acid was added 110 mg (0.636 mmol) of anhydrous manganese diacetate. The flask was loosely stopped and the solution stirred magnetically in the dark at 23° C. The course of the reaction was followed spectrophotometrically. After 24 hours, no red fluorescence of the free-base porphyrin starting material was observed, and the glacial acetic acid was removed at 50° C. in vacuo. The residue was dissolved in 300 mL of ether and washed with 300 mL of water four times. The ether solution was dried over sodium sulfate, filtered, and evaporated to give the product in quantitative yield. The dipotassium salt was prepared by dissolving the Mn-BOPP diacid in a 70% solution of tetrahydrofuran and water and passing it through a column containing Dowex 50×2–400 cation exchange resin in the K$^+$ form. The colored eluate was evaporated to dryness, redissolved in a 30% solution of tetrahydrofuran and water, and passed through a column containing freshly generated resin. (We now prefer acetone instead of THF.) The eluate was evaporated in vacuo to give a quantitative yield of the water-soluble dipotassium salt form of Mn-BOPP. This material contains approximately 3–5% water by weight. The anhydrous molecular weight of this material (with acetate as the counter ion) is 1,517.6. The purity is more than 99.9%.

EXAMPLE 7

Recombinant Protein Preparation. Recombinant HIV-1 protease (HIV-1 PR) was expressed and purified from E. coli strain D1210 using the pSOD/PR179 vector. Recombinant HIV-2 protease (HIV-2 PR) and SIV protease (SIV PR) were expressed and purified from strain X90 using pTacTac vectors.

Enzyme Assays. HIV-1, HIV-2, and SIV PRs were assayed against the decapeptide corresponding to the HIV-1 PR C-terminal autoprocessing site, by means of a discontinuous HPLC assay. Recombinant human renin and porcine pepsin were obtained and assayed using standard conditions. Bovine cathepsin D and its chromogenic substrate were purchased from Sigma. The enzyme was assayed by standard methods.

Stock solutions of the porphyrin derivatives (1 μM–10 mM) in 100% DMSO were used in IC$_{50}$ determinations. Since many of the derivatives were insoluble in buffer alone, including the free acid forms of the carborane compounds, DMSO was used to increase solubility and allow a comparison of the binding affinity. Compounds were added to buffer solutions containing additional DMSO to give a final concentration of 5%. Control reactions contained 5% DMSO only. Enzymes were preincubated with inhibitor for 1 minute at 25° C., followed by addition of substrate to initiate the reaction. As earlier noted, assays were also carried out in the absence of DMSO, when possible. Dipotassium salts of several of the inhibitors were soluble in aqueous solution and were assayed in the absence of DMSO for K$_1$ and IC$_{50}$ determinations. These IC$_{50}$ data (μM) are as follows:

| Inventive Embodiment | IC$_{50}$ μM | |
|---|---|---|
| | HIV-1 PR | HIV-2 PR |
| 1 | 0.05 | 0.230 |
| 3 | 0.10 | 0.70 |
| 4 | 0.90 | 0.550 |
| 5 | 0.725 | 0.470 |

The salt dependency of inhibition of HIV-1 PR by inventive embodiment 3 was also tested by varying the [NaCl] from 1M to 0.3M in the assay buffer, which showed the inhibition was not highly dependent on salt concentration.

Ex vivo Assay of HIV-1 Polyprotein Processing. COS A6 cells were the result of stable integration of the vector HIV-gpt by transfection of COS-7 cells. This SV40-based vector consists of the HIV-1 HXB2 strain proviral genome where the gp160 sequences were replaced by the guanidyl phosphate ribosyltransferase (gpt) gene. Following transfection, the cells were placed under selection for gpt expression by adding mycophenolic acid to the media. Surviving cells were later cloned and assayed for expression of gag p24 protein by ELISA and Western blots of culture supernatants and whole cell extracts. The cloned COS A6 cell line was maintained in DME H21 supplemented with 10% dialyzed and refiltered fetal calf serum (FCS), antibiotics (100 U/ml penicillin G, 100 μg/ml streptomycin sulfate), hypoxanthine (14 μg/ml), xanthine (250 μg/ml), and mycophenolic acid (25 μg/ml), at 37° C. and 5% $CO_2$.

MTT Cell Viability Assay. Cell survival was assessed by a quantitative colorimetric assay. The tetrazolium salt 3-(4, 5-dimethylthiazol-2-yl)2,5-diphenyltetrazolium bromide (MTT) is cleaved by dehydrogenases in active mitochondria of living cells to yield a change in color from yellow to purple. To obtain the $LD_{50}$ values for each compound, the concentration was determined at which the absorbance at 550–570 nm was half of that for the untreated cells. Compounds were tested in duplicate, in serial dilutions generally ranging from 10–250 μM concentrations in the presence of 0–0.1% DMSO. MTT assays were carried out in both the presence and absence of 10% FCS.

Effect of Albumin on Efficacy of Boronated Porphyrins. Since porphyrin compounds are known to bind to albumin, we tested the effect of fetal calf serum on the ability of inventive embodiment 1 to inhibit HIV-1 PR in vitro. Since growth and viability of COS A6 cells requires at least 2% FCS in culture medium for incubations longer than 1 hour, we chose to test the effect of porphyrin compounds on polyprotein processing using a pre-adsorption step in Dulbecco's phosphate-buffered saline (PBS), as described below.

Treatment of COS A6 Cells with Boronated Porphyrins. Cells were grown to 75% confluency in 10 cm dishes and rinsed with warm PBS. The appropriate dilution of the compounds was prepared by adding 2.5 ml of warm PBS to 2.5 μl of a stock solution prepared in neat DMSO. This material was carefully added to the cells for a 15 minute incubation. Next 2.5 ml of DME media containing 10% FCS and the appropriate compounds were added for 3.75 hours, after which time the culture supernatant was removed for isolation of viral capsids.

Viral Capsid Isolation by Ultracentrifugation. The culture supernatants were spun 10 minutes at 3,000 rpm to remove any precipitate or cell debris. The resulting supernatant was layered over a cushion consisting of 75 μl of 60% sucrose in PBS overlayed with 4 ml of 20% sucrose in PBS. The sample was spun in an SW51 Beckman rotor for 1.5 hours at 35K rpm and 4° C. Since viral capsids band at the interface of the 20 and 60% sucrose solutions, the bottom 500 μl of solution were collected.

p24 Core Antigen ELISA Assay. An ELISA kit (catalog # NEK-060) purchased from NEN/Dupont was used to determine the amount of p24 present in the viral capsid samples. This assay specifically detects p24 but not its precursors. The assay was carried out using the manufacturer's instructions. Values obtained were used to calculate the ex vivo $IC_{50}$, i.e., concentration of compound that reduces the amount of detectable p24 antigen by 50%.

The results of these studies are summarized by Table 3.

TABLE 3

| Inventive Embodiment | $IC_{50}$ in vitro[a] μM HIV-1 | μM HIV-2 | $LD_{50}$[b] μM |
|---|---|---|---|
| 1 | 0.185 | 0.70 | 25 |
| 2 | 0.275 | 1.0 | 75 |
| 3 | 0.40 | 1.2 | 70 |
| 4 | 0.70 | 1.55 | 25 |

TABLE 3-continued

| Inventive Embodiment | $IC_{50}$ in vitro[a] μM HIV-1 | μM HIV-2 | $LD_{50}$[b] μM |
|---|---|---|---|
| 5 | 0.975 | 2.2 | 80 |
| 6 | 2.25 | 1.5 | 150 |
| 7 | 5 | 13 | 250 |
| 8 | 7 | 18 | >250 |
| 9 | 12 | 11 | 250 |
| 10 | 14 | 30 | 250 |
| 11 | 14 | 23 | 250 |
| Comparative | | | |
| 12 | 280 | 480 | 250 |

[a]Determined in the presence of 5% DMSO since as previously noted, some of the derivatives were insoluble in buffer alone; however, as earlier shown for inventive embodiments 1, 3, 4, and 5, better inhibition, particularly for inventive embodiment 1, was obtained in another series of experiments where assays were conducted in the absence of DMSO.
[b]Cytotoxicity towards COS A6 cells cultured in the absence of FCS.

As exemplified and illustrated by the data of Table 3, the tetrakiscarborane carboxylate ester of 2,4-(α,β-dihydroxylethyl)deudero-porphyrin IX (that is, inventive embodiment 1) was shown to inhibit HIV-1 and HIV-2 proteases with $IC_{50}$ values of 50 and 230 nM, respectively. This particularly preferred embodiment has at least a sixty-fold greater affinity for HIV-1 PR than for cellular aspartyl proteases, as is shown by Table 4, which data was collected in the absence of DMSO.

TABLE 4

| $IC_{50}$ for Inventive Embodiment 1 on Viral and Cellular Aspartyl Proteases | |
|---|---|
| Protease | $IC_{50}$, μM |
| Renin | 3 |
| Cathepsin D | 10 |
| Pepsin | 4 |
| HIV-1 | 0.05 |
| HIV-2 | 0.23 |
| SIV | 0.25 |

FIG. 1 is a Dixon plot of inventive embodiment 5 (which is a representative example of the other embodiments) in inhibition of HIV-1 protease, where purified HIV-1 protease ($6 \times 10^{-1}$ mg/ml) was incubated with the inventive inhibitor in 50 mM sodium acetate buffer, pH 5.5, containing 1 mM dithiothreitol, 1 mM EDTA, and 1M NaCl. After 1 minute, the substrate peptide was added to give the final substrate concentrations shown. The assay solutions were incubated for 30–45 minutes at 37° and enzyme activity was determined by quantitation of the hydrolysis products on HPLC.

The importance of the FIG. 1 results are in showing the mode of binding by the embodiment to the enzyme. Thus, the inventive embodiment binds to the active site of the protease.

Cytotoxicity of compounds ($LD_{50}$) and their ability to inhibit capsid protein processing ex vivo during 4 hour incubations ($IC_{50}$) were studied. A plasmid which encodes the HIV-1 proviral genome, with the exception of the gp 150 envelope protein, was stably introduced into the monkey cell line COS 7. Cloned progeny, COS A6 cells, constitutively release viral capsids into the media. Inhibition of polyprotein processing was determined by measuring the amount of p24 present in the viral capsid samples with an ELISA assay. The decrease in the amount of detectable p24 antigen correlated with a specific inhibition of HIV PR activity, judged by the accumulation of capsid precursor in conjunction with a disappearance of the p24 mature protein band in Western blots. The MTT stain assay was used to obtain $LD_{50}$ values for all the compounds tested.

We have observed that the presence of albumin prevents the ability of the compounds to inhibit HIV-1 PR during the short-term incubations (0.25–4 hour); therefore, the $IC_{50}$ values were determined in the presence of a reduced concentration of fetal calf serum (FCS). However COS A6 cells require 10% FCS for optimal growth and viability and certain porphyrin derivatives show cytotoxicity towards COS A6 cells at <100 μM concentrations when cultured in the absence of FCS. Cytotoxicity is reduced by culturing COS A6 cells in 10% FCS. Under these conditions, the $LD_{50}$ for embodiments 1–11 is >250 μM. Compound 1 has similar $LD_{50}$ values in C6 glioma and V79 CHO cells (100–125 μM and ≧150 μM, respectively) in the presence of FCS, as measured by standard colony survival techniques. Moreover, embodiment 1 is tolerated in mice at doses as high as 200 mg/kg, with no apparent signs of morbidity or mortality of animals. Mice receiving embodiment 1 at 100 mg/kg by i.v. bolus are exposed to peak plasma concentrations of approximately 900 μM. The antagonistic effect of albumin in cell culture may not reflect the situation in whole animals, where serum proteins can bind porphyrins and deliver them to various tissues rather than sequestering them.

Inventive embodiment 1 is approximately 5-fold more effective for HIV-1 PR than for the closely related HIV-2 and SIV PRs, and at least 60-fold more inhibitory for HIV-1 PR compared to cellular aspartyl proteases (as shown in Table 4).

In sum, we have found that certain substituted porphyrins are inhibitors of retroviral aspartyl proteases, such as HIV-1 PR and HIV-2 PR, and inhibit polyprotein processing in cell culture, yet inhibition is selective over cellular aspartyl proteases.

EXAMPLE 8

We will sometime refer to Inventive Embodiment 3 as "Mn-BOPP." This embodiment was prepared as described by Example 6B. The rat brain tumor cell line 9L (designated 9L-72) was obtained from Denise Deen, Ph.D., of the Brain Tumor Research Center, University of California, San Francisco. Cells were maintained in Dulbecco-modified minimum essential medium containing 5% fetal bovine serum and 5% calf serum. Cultures were renewed from frozen stocks approximately monthly.

Fischer 344 rats (Harlan-Sprague-Dawley, Indianapolis, Ind.) (three to five for each experiment) weighing approximately 300 g were anesthetized by intramuscular injection of ketamine and xylazine (66.7 and 6.7 mg/kg body weight, respectively). After induction of surgical anesthesia, animals were placed in a stereotaxic frame. A midline incision was made, and the scalp was reflected. A small burr hole was drilled 2 mm anterior and 2.4 mm lateral to the bregma. A sharp 26-gauge Hamilton syringe was lowered to a depth of 4.5 mm, and 9L cells ($5 \times 10^4$ cells in 1.5 μL of saline) were injected over a period of two minutes. After injection, a small fragment of gelatin sponge (Gelfoam; Upjohn, Kalamazoo, Mich.) was placed in the burr hole and the scalp was sutured. All animal work was performed according to protocols reviewed and approved by the Laboratory Animal Care Committee, State University of New York, Buffalo.

MR imaging was performed on a Signa Advantage 1.5-T whole-body clinical imager (GE Medical Systems, Milwaukee, Wis.) with a custom-built transceiver rat head coil and stereotaxic head holder (detailed information to be published separately). All images were obtained with a T1-weighted spin-echo sequence, with a TR of 400 msec, a TE of 20 msec (400/20), a 3-mm section thickness, an 8-cm field of view, and a 256×256 matrix.

The ultraviolet-visible spectral data for the Mn-BOPP shows the Soret band at 368 nm ($\epsilon = 5.9 \times 10^4$). Mn-BOPP was dissolved in 0.9% sodium chloride to a concentration of 10 mg/mL and administered intravenously to the rats at a dose of 0.02 mmol/kg. Rats with 12-day-old tumors were anesthetized with an intramuscular injection of ketamine and xylazine (66.7 and 6.7 mg/kg body weight, respectively), and their heads were positioned in the head holder. Initially, a sagittal locator section was obtained. The coronal sections were graphically prescribed from the sagittal locator. The coronal plane is defined as the longitudinal section dividing the body into dorsal and ventral parts (also referred as the horizontal plane). The rats were then imaged in the coronal plane before and within 5 minutes after the administration of the metalloporphyrin compounds. Subsequent images were also obtained at various times over a period of 2–4 days.

Research software on the Signa imager provides values for the mean signal intensity and the standard deviation measured from a user-defined region of interest of a specific anatomic area on the images. Signal intensities of the tumor region and the corresponding normal brain region in the right hemisphere were measured on all images. The difference in signal intensity between the tumor and normal brain was expressed as $(SI_{tumor} - SI_{normal})/SI_{normal} \times 100$, the percent contrast enhancement of the tumor.

The T1 values of Mn-BOPP in water were measured at 0.25 T. The values for the molar relaxivity of Mn-BOPP evaluated from the slopes of the plot of relaxation rates (1/T1) versus concentrations, are 3.60 and 4.43 $L.mmol^{-1}.sec^{-1}$ at 25° C. and 37° C. respectively.

Rats were imaged before and after administration of Mn-BOPP. The glioma was apparent on the precontrast control image as a slightly hyperintense area semicircumscribed anteriorly by a hypointense crescent in the frontal region of the left hemisphere. The posterior margin of the tumor was nearly isointense to normal tissue. The immediate postcontrast image showed the tumor as slightly enhanced and the blood pool was substantially enhanced, most notably along the midline and medial margin of the tumor and extending anteriorly between the hypointense border of the tumor and posteriorly to the olfactory bulb. The subsequent image obtained at 24, 40, 69, and 92 hours showed that Mn-BOPP was retained in the tumor and that the tumor mass appeared homogeneously enhanced. Mn-BOPP is able to delineate clearly an apparent tumor boundary and to markedly enhance contrast between tumor and normal brain. The plot of percent difference in signal intensity between tumor and normal brain tissue versus time is shown in FIG. 2. The maximal enhancement of contrast between tumor and normal brain with Mn-BOPP was observed at 24 hours after injection.

These results clearly demonstrate the accumulation and selective retention of manganese in tumor. The Inventive Embodiment 3 compound is therefore an effective tumor-specific contrast agent. Thus, the metallo-complexes of this invention are not only useful for neutron capture therapy, but the particularly preferred transition metal embodiments, such as the Mn-BOPP, are further useful for MR contrast enhancement.

Inventive Embodiment 3 was effective at very low doses. For rats injected with Mn-BOPP at a dose of 0.02 mmol/kg the porphyrin was observed in the urine as a early as 15 minutes after injection. However, despite the low dose, the tumors were markedly enhanced and achieved a level of contrast that clearly delineated tumor from normal brain tissue. This tumor enhancement was observed after about 15 minutes, although Mn-BOPP was clearly seen in the blood pool of the brain within 5 minutes after injection.

In addition to the advantage of increased tumor conspicuity with well-defined tumor/normal brain tissue border and the possible delineation of edema and necrosis, signal enhancement will show the tumor/selective delivery of this boronated compound to tumor sites for therapeutic purposes. The inventive embodiment 3 is an MR contrast agent with dual functions of diagnosis and therapy.

It is to be understood that while the invention has been described above in conjunction with preferred specific embodiments, the description and examples are intended to illustrate and not limit the scope of the invention, which is defined by the scope of the appended claims.

It is claimed:

1. A porphyrin-based compound having the structure:

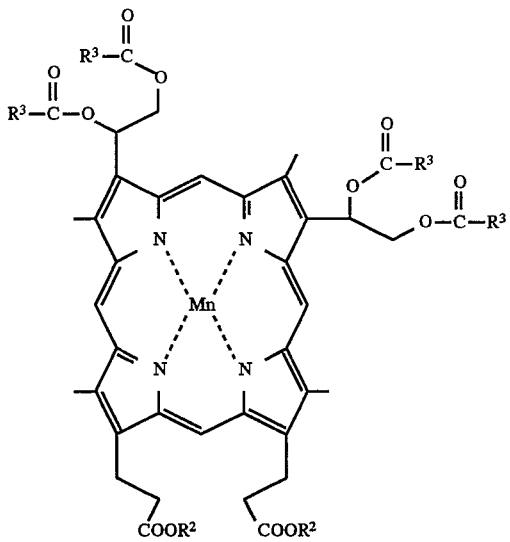

where $R^3$ is a carborane and $R^2$ is an alkyl or an aryl having 1 to about 7 carbon atoms, or a physiologically acceptable salt thereof.

2. The compound as in claim 1 wherein $R^3$ is a closo-carborane.

3. The compound as in claim 2 wherein the carborane is a substituted or unsubstituted 1,2-icosahedral isomer (1,2-$C_2B_{10}H_{12}$).

4. The compound as in claim 2 wherein the carborane is a substituted or unsubstituted 1,7-icosahedral isomer (1,7-$C_2B_{10}H_{12}$).

5. The compound as in claim 2 wherein the carborane is enriched in $^{10}$boron.

6. The compound as in claim 1 wherein the carborane is enriched in $^{10}$boron.

7. A biologically active, porphyrin-based compound having the structure:

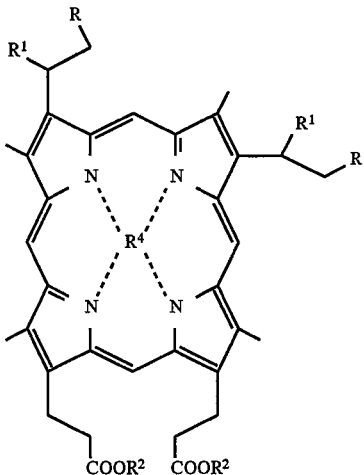

where each of R and $R^1$ is selected from —H, —OH, or

and at least one of R and $R^1$ is

$R^3$ is a carborane, $R^2$ is —H, an alkyl, or an aryl, having 1 to about 7 carbon atoms, or a physiologically acceptable salt thereof, and $R^4$ is manganese, copper or cobalt.

8. The compound as in claim 7 where $R^4$ is manganese and the compound has the biological activity of accumulating in tumors.

* * * * *

UNITED STATES PATENT AND TRADEMARK OFFICE
CERTIFICATE OF CORRECTION

PATENT NO. : 5,654,423
DATED : August 5, 1997
INVENTOR(S) : Kahl et al.

It is certified that error appears in the above-indentified patent and that said Letters Patent is hereby corrected as shown below:

In Column 8, line 3:
replace "Synthesis of 2,4-bis-[α,β-(2-dicarbaclosododecaborane" with:

--Synthesis of 2,4-bis-[α,β-(1,2-dicarbaclosododecaborane--

In Column 10, replace TABLE 1 with TABLE 1 attached

In Column 10, line 28:
replace "group: the porphyrin (ring current) and carboranyl acyl (σ effects)."

--groups: the porphyrin (ring current) and carboranyl acyl (σ effects).--

In Column 10 and 11, replace TABLE 2 with TABLE 2 attached

Signed and Sealed this

Twenty-first Day of April, 1998

Attest:

Attesting Officer

BRUCE LEHMAN

Commissioner of Patents and Trademarks

TABLE 1*

| δ | multiplicity | assignments |
|---|---|---|
| 10.27, 10.23, 10.16, 10.14 | s, 4H | meso H |
| 7.68 | m, 2H | α CH |
| 5.68; 4.99 | m, 4H | β $CH_2$ |
| 4.41 | m, 4H | Por-$CH_2$ |
| 4.17; 4.10 | s, 4H | carborane CH |
| 3.81; 3.80 | s, 6H | $CO_2CH_3$ |
| 3.68; 3.64 | s, 12H | β-$CH_3$ |
| 3.63; 3.61 | | |
| 3.30 | m, 4H | -$CH_2CO_2R$ |
| -3.65 | s, 2H | NH |

* N.M.R. spectrum was recorded in $CDCl_3$ (ca. $5 \times 10^{-3}$ M) at 300 MHz at ambient temperature with TMS internal reference.

TABLE 2

| Inventive Embodiment | R | $R^1$ | $R^4$ |
|---|---|---|---|
| 1 | $OCOB_{10}H_{11}C_2$ | Same as R | $H_2$ |
| 2 | H | $OCOB_{10}H_{11}C_2$ | $H_2$ |
| 3 | $OCOB_{10}H_{11}C_2$ | Same as R | Mn(III) |
| 4 | $OCOB_{10}H_{14}C_3$ | Same as R | $H_2$ |
| 5 | $OCOB_{10}H_{11}C_2$ | Same as R | Cu(II) |
| 6 | $OCOB_{10}H_{11}C_2$ | Same as R | Co(II) |
| 7 | OCO(adamantoyl) | Same as R | $H_2$ |
| 8 | OCOp-[$(CH_3)_2$N]benzoyl | Same as R | $H_2$ |
| 9 | meta-$OCOB_{10}H_{11}C_2$ | Same as R | $H_2$ |
| 10 | $OCOC_6H_5$ | Same as R | $H_2$ |
| 11 | OCO($\beta$-naphthoyl) | Same as R | $H_2$ |

Comparative

| | | | |
|---|---|---|---|
| 12 | OH | OH | $H_2$ |